(12) United States Patent
    Clark

(10) Patent No.: US 11,744,221 B2
(45) Date of Patent: *Sep. 5, 2023

(54) GRAPE PLANT NAMED 'COMPASSION'

(71) Applicant: THE BOARD OF TRUSTEES OF THE UNIVERSITY OF ARKANSAS, Little Rock, AR (US)

(72) Inventor: John Reuben Clark, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/573,555

(22) Filed: Sep. 17, 2019

(65) Prior Publication Data

US 2020/0084992 A1    Mar. 19, 2020

Related U.S. Application Data

(60) Provisional application No. 62/732,250, filed on Sep. 17, 2018.

(51) Int. Cl.
   *A01H 6/88*    (2018.01)
   *A01H 5/08*    (2018.01)

(52) U.S. Cl.
   CPC .............. *A01H 6/88* (2018.05); *A01H 5/08* (2013.01)

(58) Field of Classification Search
   CPC ........................................................ A01H 6/88
   USPC ................................................. Plt./205–207
   See application file for complete search history.

(56) References Cited

U.S. PATENT DOCUMENTS

| | | | | |
|---|---|---|---|---|
| PP5,013 P | * | 3/1983 | Olmo | ............... A01H 6/88 Plt./207 |
| PP13,309 P2 | | 12/2002 | Clark et al. | |
| PP25,152 P3 | | 12/2014 | Clark et al. | |
| PP25,696 P3 | | 7/2015 | Clark et al. | |
| PP25,697 P3 | | 7/2015 | Clark et al. | |
| PP25,726 P3 | | 7/2015 | Clark et al. | |
| PP25,746 P3 | | 7/2015 | Clark et al. | |
| PP31,526 P2 | * | 3/2020 | Clark | ............... A01H 6/88 Plt./207 |

OTHER PUBLICATIONS

Clark et al. HortScience vol. 53, No. 3, pp. 401-403 Mar. 2018 (Year: 2018).*
Vouillamoz et al Heredity vol. 97, pp. 102-110 (Year: 2006).*
Vance et al. Journal of the American Pomological Society vol. 71, No. 4, pp. 240-249 Oct. 2017 (Year: 2017).*
Clark, J.R. et al. "'Compassion' Seedless Table Grape" 2018 Hortscience 53(3):401-403. 2018. https://doi.org/10.21273/HORTSCI12783-17.
Vance, A.J. et al. "Table Grape Cultivar Performance in Oregon's Willamette Valley" 2017 Journal of the American Pomological Society 71(4): 240-249.
Shan, F. et al. "Semi-sterilized Tissue Culture for Rapid Propagation of Grapevines (*Vitis vinifera* L.) Using Immature Cuttings." HortScience 49.7 (2014): 949-954.

* cited by examiner

*Primary Examiner* — David H Kruse
(74) *Attorney, Agent, or Firm* — Quarles & Brady, LLP

(57) ABSTRACT

A grape plant designated as 'Compassion' or a progeny thereof are provided herein. Also provided are pollen, tissues or cells of the plant. The plants or plant parts may be used for breeding or creating transgenic plants. Products made using the grapes of the plant are also provided.

20 Claims, 3 Drawing Sheets
(3 of 3 Drawing Sheet(s) Filed in Color)

GRAPE PLANT NAMED 'COMPASSION'

CROSS-REFERENCE TO RELATED PATENT APPLICATIONS

The present application claims the benefit of priority to U.S. Provisional Patent Application No. 62/732,250, filed on Sep. 17, 2018, the contents of which are incorporated herein by reference in its entirety.

INTRODUCTION

The genus *Vitis* is an economically important source of grapes for direct consumption (table grapes), wine production (wine grapes), and the manufacturing of several grape-based products such as raisins, juice, jams, and jellies. While both table grape and wine grape cultivars belong to the same species, these cultivars have been bred to have significantly different fruit characteristics. Wine grapes tend to be smaller and have seeds and thicker skins. On the other hand, table grape plants tend to be larger and have thinner skins and lack seeds.

The growth and yield of table grape cultivars depends on various environmental factors, including soil type and climate. For example, poor fruit set due to cool, wet weather during bloom can reduce yield and lead to excessively loose clusters. Grape powdery mildew can also damage all parts of a grape plant, including the fruit, and causes "off" flavors. Furthermore, the presence of seed traces in seedless cultivars, typically an undesirable trait for consumers, can vary among berries within a cultivar depending on weather during the growing season.

Accordingly, there is a need in the art for new grape cultivars that are adapted to a particular climate and produce grapes that have favorable taste and morphological characteristics.

SUMMARY

In one aspect of the present invention, grape plants are provided. The grape plants may include the grape plant designated as A-2932 ('Compassion'), or parts, modified versions, or progeny thereof. In some embodiments, the grape plants may include a grape plant including all of the physiological and morphological characteristics of the grape plant described herein. A sample of cells of this grape plant will be deposited with a depository certified under the terms of the Budapest treaty.

In another aspect, the present invention relates to a tissue culture of cells. The tissue culture of cells may be produced from a protoplast or a cell from a 'Compassion' grape plant, a modified 'Compassion' grape plant, or parts or progeny thereof.

In another aspect of the present invention, methods for producing a grape plant are provided. The methods may include crossing any one of the 'Compassion' grape plants or modified 'Compassion' grape plants described herein with itself or a second different grape plant, and harvesting the resultant seed or embryo. Optionally, the methods may further include growing the seed or embryo into a mature grape plant.

In a further aspect, the present invention relates to methods of producing a transgenic grape plant. The methods may include introducing an exogenous polynucleotide conferring resistance to a herbicide, a pest, an insect, or a disease into the 'Compassion' grape plant, or part or progeny thereof.

In a still further aspect of the present invention, methods of producing a grape plant product are provided. The methods may include obtaining any one of the modified or unmodified 'Compassion' grape plants described herein, or parts or progeny thereof, and producing the grape plant product.

BRIEF DESCRIPTION OF THE DRAWINGS

The patent or application file contains at least one drawing executed in color. Copies of this patent or patent application publication with color drawings will be provided by the Office upon request and payment of the necessary fee.

The accompanying photographs show typical specimens of the new variety in color as nearly true as it is reasonably possible to make in a color illustration of this character. The photographs provided herein are of 10 year old vines.

DETAILED DESCRIPTION

Figure 1:
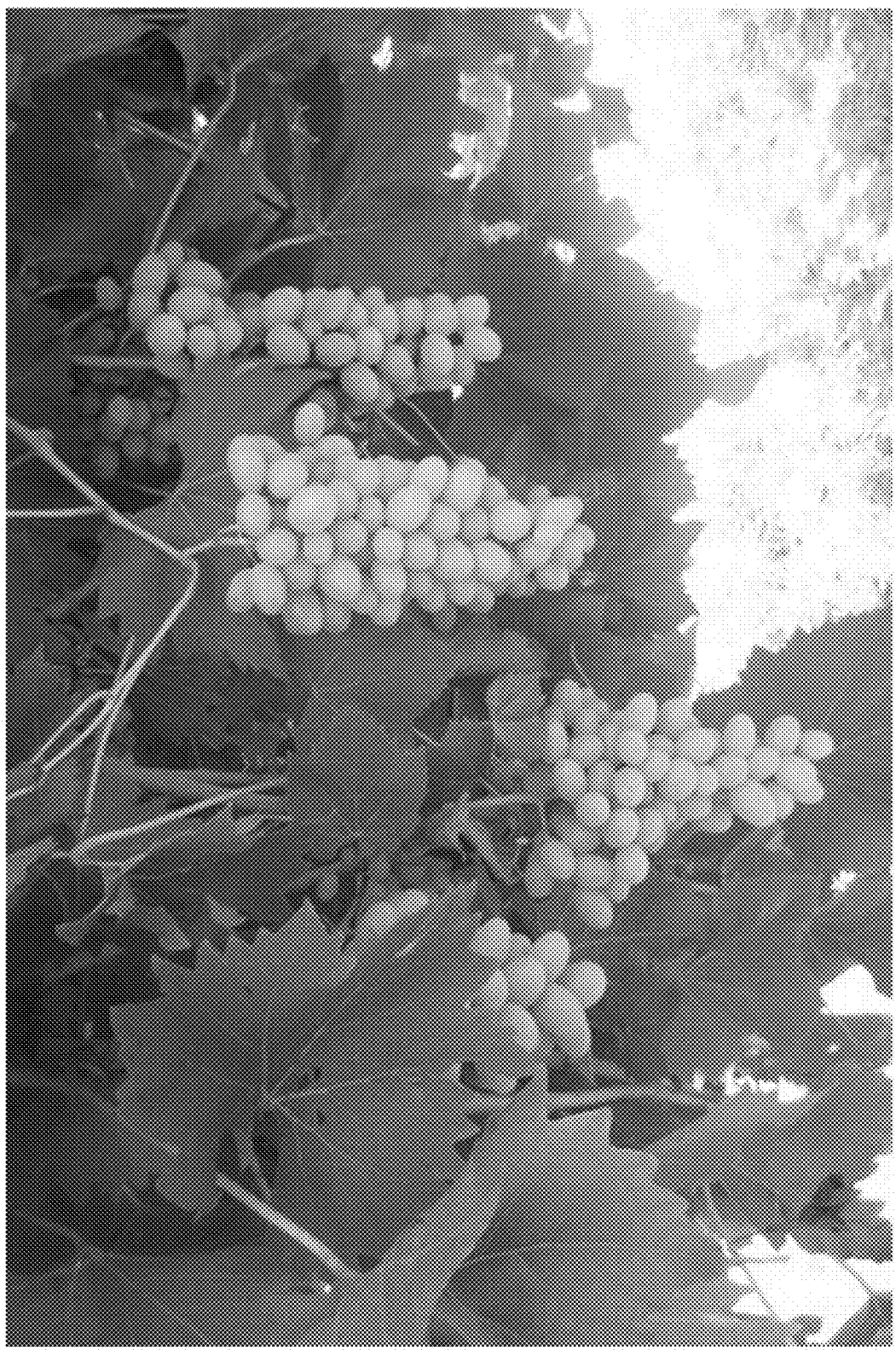
FIG. 1 is a photograph showing typical clusters of healthy fruit, near Clarksville, Ark.

The present inventors disclose herein a new and distinct cultivar of table grape plant designated as A-2932 ('Compassion'). A tissue culture sample of the new cultivar has been deposited under the terms of the Budapest Treaty with the Bigelow Laboratory for Ocean Science Patent depository under Accession No. 202302014. The new cultivar is a green (white), seedless table grape variety which provides a significant advancement in fruit crispness and firmness beyond previous Arkansas developments along with having an exquisite fruity flavor and limited fruit cracking or skin splitting in the Arkansas environment. The 'Compassion' cultivar was selected for its potential as a table grape for utilization in the mid- to upper-South of the United States and other areas of similar climate.

The 'Compassion' cultivar of grapevine originated from a hand-pollinated cross of 'Ark. 2349' (non-patented, non-released breeding genotype; female parent)×'Ark. 2304' (non-patented, non-released breeding genotype; male parent) made in 2002 near Clarksville, Ark. The seeds resulting from this controlled hybridization were germinated in a greenhouse during the winter of 2002-03. Resulting seedlings were planted in the spring of 2003 in a vineyard near Clarksville, Ark. The seedlings fruited in the summer of 2006 and one seedling, designated 'Arkansas Selection 2932,' was selected for its potential for fresh-market production as a seedless table grape.

During late 2006 and early 2007, the original plant selection was propagated asexually at the above-noted location, by rooting hardwood cuttings. A test planting of three vines was established. In all propagations, hardwood cuttings were used and the selection rooted readily from hardwood cuttings. All propagules (resulting plants) of the new cultivar have been observed to be true to type in that during all asexual multiplication, the vegetative and fruit characteristics of the original plant have been maintained. All vines planted from hardwood cutting propagation fruited in the second or third season of growth in the vineyard after planting.

Vines of the new cultivar have good growth, not being excessively vigorous and good health as exhibited by good leaf color and no to minimal disease presence. It has produced well as own-rooted plants in all testing and has not been evaluated on any rootstocks. Adaptation to the Arkansas test site is very good as winter injury and heat damage were minimal.

The health of the 'Compassion' cultivar is good. Vines were evaluated for presence of the following diseases: powdery mildew (*Erysiphe necator* Schw. (syns. *Uncinula necator* (Schw.) Burr., *E. tuckeri* Berk., *U. americana* Howe, and *U. spiralis* Berk. & Curt; anamorph *Oidium tuckeri* Berk.), downy mildew (*Plasmopara viticola* Berl. & de Toni.), anthrancnose (*Elsinoë ampelina* Shear), and black rot (*Guignardia bidwellii* Viala & Ravaz). The 'Compassion' cultivar is moderately resistant to powdery mildew, downy mildew, and anthrancnose, but susceptible to black rot. All of these diseases can be controlled by the use of available fungicides.

The 'Compassion' cultivar's average harvest date is August 22nd in Arkansas. The berries are medium (ca. 4.5 g) and elongated-oval in shape. See FIG. 1. Fruit is seedless with small residual seed traces in most years. Fruit texture is a non-slipskin type and is crisp and firm. Flavor is fruity with some muscat aspects included and average soluble solids of 20%. Fruit cracking and skin splitting is limited though some may be seen in severe rainfall pressure seasons. Medium-sized to large clusters are well-filled to tight with average cluster weight being 470 g in Arkansas. See FIG. 1. Yield average in Arkansas is 11.4 kg/vine.

'Compassion' differs from its female parent Ark. 2349 in that 'Compassion' is seedless, has fruit cracking resistance, has greater yield potential and is green rather than red.

'Compassion' differs from it male parent Ark. 2304 in that it has fruit cracking resistance, better plant health and larger clusters.

Table 1 provides a detailed description of the botanical and pomological characteristics of the 'Compassion' cultivar. The descriptions reported herein, including Table 1, are from specimens grown near Clarksville, Ark. Vines used for measurement were 10 years old and were irrigated using trickle (drip) irrigation. Vines were fertilized annually in spring with Nitrogen or complete fertilizers. No shoot or leaf thinning practices were conducted on the vines. No girdling or gibberellic acid application practices were carried out on the vines. The color data in Table 1 are presented in Royal Horticultural Society Colour Chart designations, 1986 version, second edition. The dimensions, sizes, colors and other characteristics described in Table 1 are approximations of averages set forth as accurately as practicable.

TABLE 1

Botanical and Pomological Characteristics of the 'Compassion' Cultivar

Vine

Size: medium.
Growth vigor: moderate.
Density of foliage: medium-thick.
Productivity: moderate yielding, 11.4 kg/vine.
Rootstock: none; own-root.
Cold hardiness: hardy to −17° C. (1° F.); potentially more hardy as this was the coldest temperature experienced at the test site.
Shoots (current-season canes)

Color of shoots (current-season canes): sun exposed side: grayed-orange group 166-A, green group 143-C (where anthocyanin present with green undercoat); shaded side: green group 143-A.
Shoot attitude: semi-procumbent.
Canes (mature, dormant, measured in winter)

Figure 2:
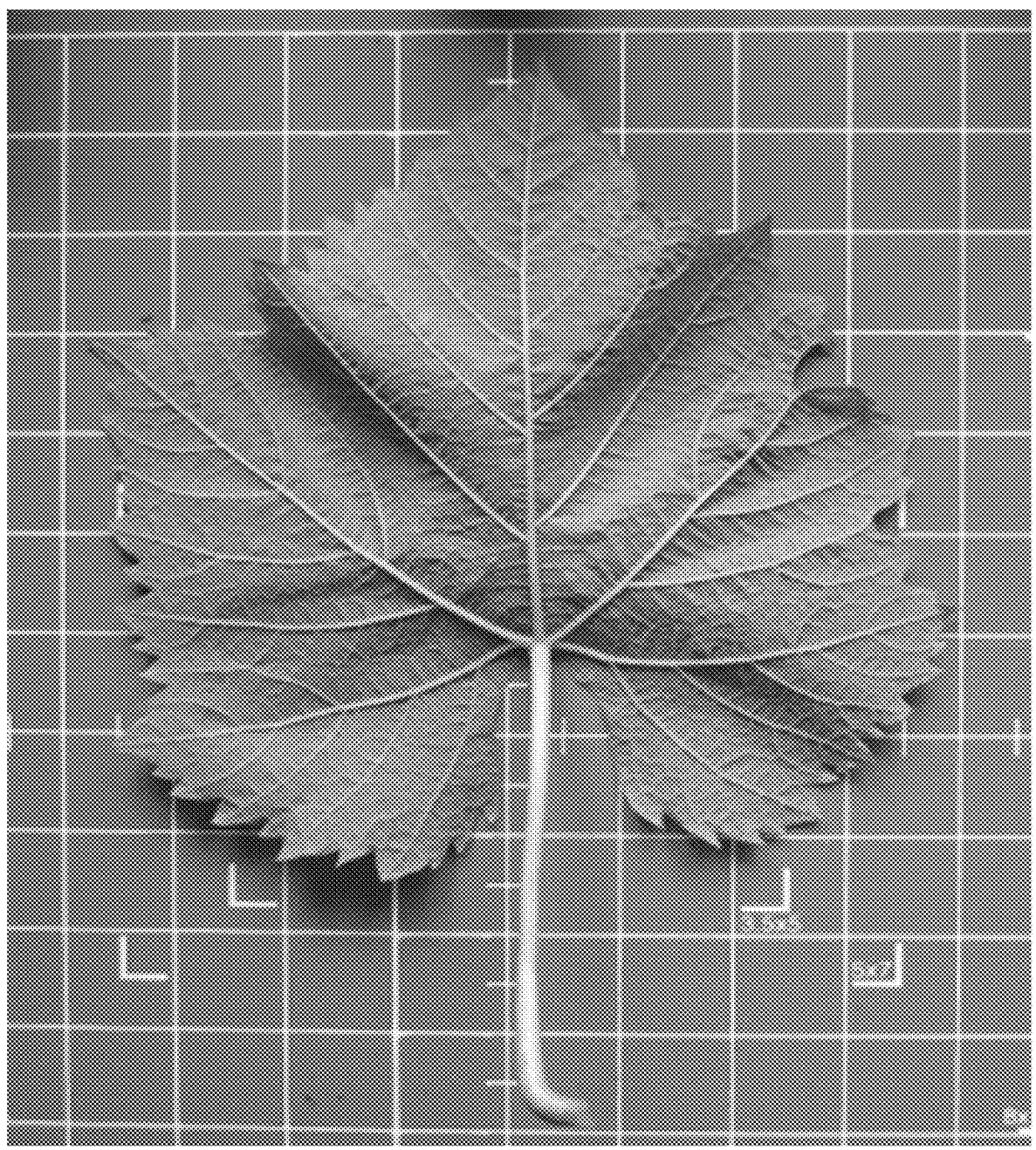
FIG. 2 is a photograph showing the leaf abaxial view, near Clarksville, Ark.
Figure 3:
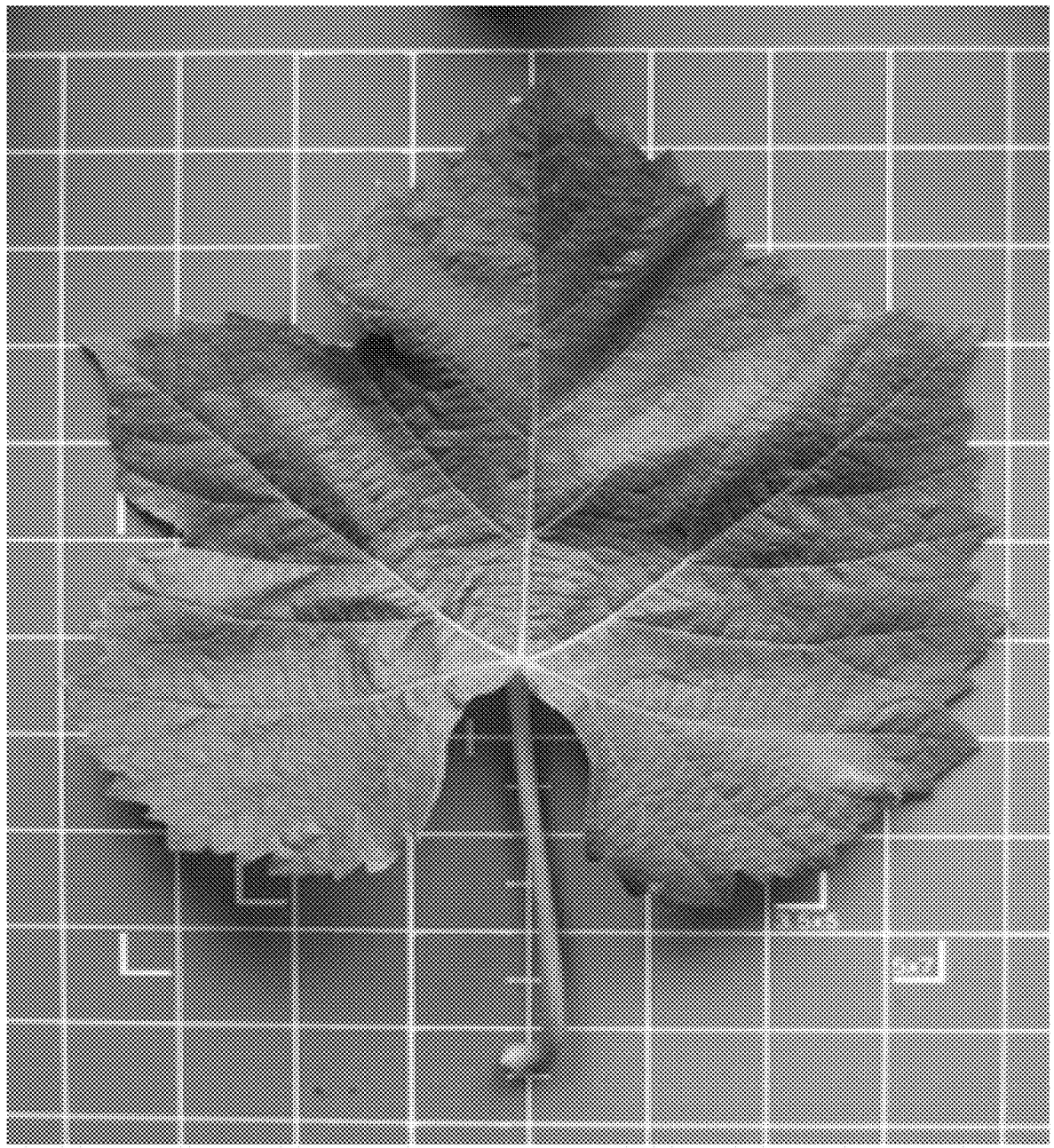
FIG. 3 is a photograph showing the leaf adaxial view, near Clarksville, Ark.

Color of mature, dormant cane: base: grayed-orange group 165-B; midpoint: grayed-orange group 165-B; terminal: grayed-orange group 164-A; anthocyanin not present on mature canes.
Texture of mature, dormant canes: smooth.
Shape of dormant canes: round to lachrymiform (tear drop).
Length of mature, dormant canes: average 1.3 m.
Diameter of mature, dormant cane: base: 1.0 cm; midpoint: 0.7 cm; terminal: 0.4 cm.
Internode length of mature, dormant canes: base: 4.4 cm; midpoint: 8.1 cm; terminal: 4.2 cm.
Lenticels: not present on mature canes.
Canes mature to tips in the fall.
Trunk Diameter at 30 cm above soil level: 3.4 cm.
Shape: roundish.
Trunk straps: present similar to other bunch grapes.
Surface texture: smooth with rough peeling (exfoliating) bark.
Color: inner bark color: grayed-orange group 165-A; outer bark color: grayed group 201-B with some grayed group 200-C on portions of bark.
Foliage (See FIGS. 2 and 3)

Arrangement of mature leaves: simple and alternate.
Shape of mature leaves: palmate.
Number of lobes on mature leaves: 3.
Petiole sinus of mature leaves: open.
Venation of mature leaves: reticulate.
Margin of mature leaves: serrated with teeth medium in size.
Teeth shape of mature leaves: straight to occasional concave.
Surface texture of mature leaves: abaxial side: very mildly corrugated; adaxial side: waxy, smooth.
Dimensions of mature leaves: length: 15.7 cm; width: 16.3 cm; thickness: 0.03 cm.

TABLE 1-continued

Botanical and Pomological Characteristics of the 'Compassion' Cultivar

Pubescence on mature leaves: abaxial side: light on veins, none to light on leaf surface; adaxial side: none.
Color of mature leaves: base abaxial: yellow-green group 146-B; base adaxial: green group 137-A; midpoint abaxial: yellow-green group 146-B; midpoint adaxial: green group 137-A; terminal abaxial: yellow-green group 146-B; terminal adaxial: green group 137-A; no anthocyanin present.
Color of veins on mature leaves: abaxial surface: yellow-green group 146-D; adaxial surface: yellow-green group 146-C; no anthocyanin on leaf veins.
Leaf pubescence on young leaves: abaxial side: lightly present veins and along edges: adaxial side: none.
Color of young leaves: base abaxial: yellow-green group 145-A (no anthocyanin present); base adaxial: yellow-green group 145-A (no anthocyanin present); midpoint abaxial: anthocyanin present, color grayed-orange group 176-C; midpoint adaxial: anthocyanin present, color grayed-orange group 176-C; terminal abaxial: yellow-green group 144-A (no anthocyanin present); terminal adaxial: yellow-green group 144-A (no anthocyanin present).
Vein color of young leaves: abaxial side: yellow-green group 147-C; adaxial side: yellow-green group 147-C; grayed-purple group 184-B (petiole end).
Texture of young leaf veins: abaxial side: heavy pubescence; adaxial side: smooth.
Petioles Color of mature petioles: yellow-green group 146-C; anthocyanin present on mature petioles exposed to sun with anthocyanin color Greyed-red group 182A. Anthocyanin intensity varies on petiole based on sun exposure with shaded sides having little to no anthocyanin.
Dimensions of mature petioles: length: 10.5 cm; diameter: 0.3 cm.
Color of young petioles: yellow-green group 146-B (no anthocyanin present).
Tendrils Found beginning on the 4th node.
Orientation: opposite.
Dimensions: length: 15.9 cm.
Texture: smooth.
Diameter: 1.2 mm
Color of mature tendril: yellow-green group 146-D.
Tendril forked.
Buds (measured in dormant season)

Number of buds on current, single-season cane: 19.
Dimension of dormant buds: width: 0.3 cm, length: 3.6 mm.
Shape of dormant buds: pyramidal.
Color of dormant buds: grayed-orange group 177-A.
Texture of dormant buds: bumpy where scales meet.
Bud break: 5 April.
Disease resistance Moderately resistant to powdery mildew, downy mildew, and anthracnose, and susceptible to black rot. Other disease susceptibilities not known.
Flower Fragrance: sweet, flowery, distinct.
Sex: hermaphrodite
Bloom Dates: first bloom: 23 May; full bloom: 25 May.
Flowers per cluster: 763.
Inflorescence dimensions: length: 18.8 cm; diameter: 4.9 cm.
Flower dimensions: length: 0.5 cm; diameter: 0.8 cm.
Flower shape: typical of *Euvitis* (bunch) grapes, with flowers having a cohering petal at summit and separating petal at base and petal reflexed after dehiscence from flower.
Flower longevity: lasts 3-5 days in full bloom.
Stamens Number: 5.
Filament color: yellow-green group 145-C.
Pistil Number: 1.
Length: 0.3 cm.
Color: yellow-green group 144-A.
Pollen Color: yellow-orange group 20-B.
Petal Number: 5.2 fused petals, form calyptra (flower cap)
Color: yellow-green group 144-A.
Sepal: none.

TABLE 1-continued

Botanical and Pomological Characteristics of the 'Compassion' Cultivar

Pedicel

Dimensions: length: 0.93 cm; diameter: 0.14 cm.
Color: top: grayed-orange group 174-A; bottom: yellow-green group 144-B.
Fruit Maturity: 22 August.
Berry shape: elongated, oval.
Berry color: skin: yellow-green group 145-A; flesh: yellow-green group 145-A.
Berry dimensions: diameter at equator: 1.7 cm; diameter at base: 1.1 cm; diameter at apex: 0.9 cm; length: 2.4 cm.
Berry weight: 4.5 g.
Berry texture: non-slipskin; crisp.
Firmness: very firm.
Skin thickness: 0.4 mm.
Tenacity: high.
Seeds: no, small residual seed traces present most years.
Brush length: 0.4 cm.
Juiciness: low.
Flavor: is fruity derived partially from *V. labrusca*, with some aspects of muscat.
Juice Soluble solids: 20.0%.
Titratable acidity: 0.58 g/L tartaric acid.
Color: yellow group 4-D.
pH: 3.4.
Seed Seedless, no seeds present
Seed traces of undeveloped seeds, number per berry: 2, very soft/edible
Cluster Weight: 470 g.
Cluster dimensions: length: 20.0 cm; width: 18.4 cm.
Berries per cluster: 128.
Cluster per vine: 30.
Clusters per shoot: 1.6.
Peduncle length: 5.0 cm.
Peduncle diameter: 4.16 mm.
Peduncle color: yellow-green group 145-A (no anthocyanin present).
Grape Plants In one aspect of the present invention, grape plants are provided. The grape plants may include the grape plant designated as A-2932 ('Compassion'), of which a tissue culture sample is deposited under the terms of the Budapest Treaty with Bigelow laboratory for Ocean Science under Accession No. 202302014, or parts, modified versions, or progeny thereof. In some embodiments, the grape plants may include a grape plant including all of the physiological and morphological characteristics of the 'Compassion' grape plant described herein.

As used herein, a "plant" includes any portion of the plant including, without limitation, a whole plant or a portion of a plant such as, without limitation, pollen, ovule, root, leaf, stem, seed, fruit, flower, tissue plant germplasm, asexual propagate, or any progeny thereof. For example, a grape plant refers to the whole grape plant or portions thereof including, without limitation, the pollen, the ovule the leaves, flowers, fruits, stems, roots, or otherwise. In some embodiments, the grape plant part may be a plant cell obtained from, without limitation, a pollen, an ovule, an embryo, a leaf, a stem, a root, a root tip, an anther, a cotyledon, a meristematic cell, a hypocotyl, a pistil, a flower, or a fruit.

As described in the Examples, the present inventors have also DNA profiled the 'Compassion' grape cultivar to facilitate more convenient identification of 'Compassion' plants and modified versions and progeny thereof. Accordingly, in some embodiments, the grape plant may include the microsatellite alleles identified in Table 2 or the microsatellite alleles identified in Table 2 and Table 3.

TABLE 2

Distinguishing Alleles Between 'Compassion' Cultivar and Parent

| Microsatellite DNA Marker | Allele 1 | Allele 2 |
|---|---|---|
| VVS2 | 125 | 135 |
| VVMD5 | 232 | 236 |
| VVMD7 | 239 | 251 |
| VVMD27 | 179 | 185 |
| VrZAG62 | 195 | 195 |
| VrZAG79 | 255 | 263 |

TABLE 3

Additional Alleles of the 'Compassion' Cultivar

| Microsatellite DNA Marker | Allele 1 | Allele 2 |
|---|---|---|
| VVMD6 | 219 | 219 |
| VVMD28 | 229 | 237 |
| VVMD31 | 204 | 214 |
| VVMD32 | 251 | 257 |

In some embodiments, the grape plant may be a grape plant clonally propagated from the 'Compassion' grape cultivar described herein or a progeny thereof.

The grape plants may also be a modified 'Compassion' grape plant. As used herein, the term "modified" refers to a) naturally-arising variants of the 'Compassion' grape cultivar described herein or a progeny thereof or b) using any laboratory methods available to those of skill in the art including, without limitation, genetic engineering techniques (i.e. CRISPR/Cas or other genome engineering techniques or transgenic methodologies) to alter the 'Compassion' grape cultivar described herein or a progeny thereof.

In some embodiments, the modified 'Compassion' grape plant may be a transgenic 'Compassion' grape plant. The transgenic 'Compassion' grape plant may be a 'Compassion' grape plant further including an exogenous polynucleotide conferring resistance to an herbicide, a pest, an insect, or a disease.

As used herein, suitable diseases may include, without limitation, powdery mildew.

As used herein, suitable herbicides may include, without limitation, glyphosate, imidazolinone, sulfonylurea, dicamba, benzonitrile, glufosinate, phenoxy proprionic acid, L-phosphinothricin, cyclohexone, cyclohexanedione, triazine, 2,4-Dichlorophenoxyacetic acid, and hydroxyphenyl-pyruvate dioxygenase (HPPD) inhibitors.

The grape plants may also be a progeny of a 'Compassion' grape plant or a modified 'Compassion' grape plant obtained by, for example, crossing a 'Compassion' grape plant or a modified 'Compassion' grape plant with another 'Compassion' grape plant, a modified 'Compassion' grape plant, or a different grape plant. As used here, the term "crossing" refers to the pollination of a female flower of a grape plant thereby resulting in the production of seed from the flower. Any plants produced using the 'Compassion' cultivar as at least one parent, grandparent, etc. are within the scope of this invention.

Tissue Culture of Cells

In another aspect, the present invention relates to a tissue culture of cells. The tissue culture of cells may be produced from a protoplast or a cell from a 'Compassion' grape plant, a modified 'Compassion' grape plant, or parts or progeny thereof. In some embodiments, the protoplast or the cell may be produced from a plant part including, without limitation, a pollen, an ovule, an embryo, a leaf, a stem, a root, a root tip, an anther, a cotyledon, a meristematic cell, a hypocotyl, a pistil, a flower, or a fruit.

Methods for Producing a Grape Plant

In another aspect of the present invention, methods for producing a grape plant are provided. The methods may include crossing any one of the 'Compassion' grape plants or modified 'Compassion' grape plants described herein with itself or a second different grape plant, and harvesting the resultant seed or embryo. Compassion's use in conventional breeding techniques would likely impart both exceptional and unique flavor in offspring, and crossing with commercial *Vitis vinifera* table grape cultivars would be a likely path for 'Compassion' to be used in breeding. Optionally, the methods may further include growing the seed or embryo into a mature grape plant.

Any methods using a modified or unmodified 'Compassion' cultivar are part of this invention. For example, selfing, backcrosses, hybrid breeding, and crosses to other grape cultivars may be included.

Crosses with the modified or unmodified 'Compassion' cultivar may be performed in two ways—with the 'Compassion' cultivar serving as the male or female parent.

As a male pollen, a 'Compassion' pollen may be applied to an ovule of second grape plant using conventional crossing methodologies.

As a female parent, however, given that the 'Compassion' cultivar is seedless grape variety, embryo rescue may be used. In this embodiment, a female modified or unmodified 'Compassion' cultivar may be pollinated with the selected pollen of the second grape plant, and after a period of embryo development, the developing "seed" or "trace" is removed from the developing berry and placed in tissue culture for expansion. The tissue culture may include a growth medium such as, without limitation, a nutrient and growth regulator tissue culture medium. Such media and techniques are known to those skilled in the art and can be found in articles such as the Intl J Plant Develop Biol (2010) 4:26-30 or Hort Sci (2014) 49: 949-954. In the tissue culture medium, the embryo is rescued and so it does not abort as it would naturally. When the embryo is mature, it may be removed from the seed trace and placed in a test tube to grow into a small plant, which is eventually planted in the field as a seedling vine.

Methods of Producing a Transgenic Grape Plant

In a further aspect, the present invention relates to methods of producing a transgenic grape plant. The methods may include introducing an exogenous polynucleotide conferring resistance to a herbicide, a pest, an insect, or a disease into the 'Compassion' grape plant, or part or progeny thereof.

As used herein, "introducing" describes a process by which exogenous polynucleotides (e.g., DNA) is introduced into a recipient cell. Methods of introducing nucleic acids into a plant cell are known in the art and may include, without limitation, transformation, particle bombardment or microinjection. Transformation may occur under natural or artificial conditions according to various methods well known in the art, and may rely on any known method for the insertion of foreign nucleic acid sequences into a eukaryotic plant host cell.

Methods of Producing a Grape Plant Product

In a still further aspect of the present invention, methods of producing a grape plant product are provided. The methods may include obtaining any one of the modified or unmodified 'Compassion' grape plants described herein, or parts or progeny thereof, and producing the grape plant product.

As used herein, a "grape plant product" may include any product produced from a grape plant. The grape plant product may be, without limitation, grapes, raisins, wine, juice, jam, jelly, paste, puree, freeze-dried fruits, or nutraceutical compositions. The grape plant product may also include at least one cell of any one of the modified or unmodified 'Compassion' grape plants described herein, or parts or progeny thereof.

Finally, grape plant products produced by these methods are also provided.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

Unless otherwise specified or indicated by context, the terms "a", "an", and "the" mean "one or more."

The following examples are meant only to be illustrative and are not meant as limitations on the scope of the invention or of the appended claims.

EXAMPLES

Example 1—DNA Profiling of A-2392 ('Compassion')

Methods

Dried leaf samples from the new grape selection A-2392 ('Compassion') and a presumptive parent grape plant (A-2304) were submitted to the Plant Identification Lab at the University of California, Davis for DNA profiling analysis. Two samples from each selection were subjected to DNA profiling analysis. The DNA profiles from the two samples of each selection matched one another as expected.

DNA from each sample was typed with 10 grape microsatellite DNA markers—VVS2, VVMD5, VVMD7, VVMD27, VrZAG62, VrZAG79, VVMD6, VVMD28, VVMD31, and VVMD32. The 6 grape microsatellite DNA markers—VVS2, VVMD5, VVMD7, VVMD27, VrZAG62, VrZAG79 were adopted by the EU Grape Genetic Resources Working Group and Foundation Plant Services at the University of California Davis DNA-based grape variety identification service as common markers to facilitate the exchange of data among grape research laboratories. The use of 10 markers provides a very high degree of confidence that the profiles obtained are unique to the selection.

Results

The two alleles identified at each microsatellite DNA marker for the A-2392 ('Compassion') selection and the A-2304 selection are shown in Table 4. In Table 4, the underlined alleles are common to both of the measured profiles. As seen in Table 4, the A-2392 ('Compassion') selection and the A-2304 selection share at least one allele at each of the ten microsatellite DNA markers, which is consistent with the A-2304 selection being a parent to the A-2392 ('Compassion') selection.

TABLE 4

DNA Profiles of the A-2392 ('Compassion') selection and the A-2304 selection

| Selection | VVS2* | VVMD5* | VVMD7* | VVMD27* | VrZAG62* | VrZAG79* | VVMD6 | VVMD28 | VVMD31 | VVMD32 |
|---|---|---|---|---|---|---|---|---|---|---|
| Compassion | <u>125</u> | 232 | <u>239</u> | <u>179</u> | <u>195</u> | 255 | <u>219</u> | <u>229</u> | <u>204</u> | <u>251</u> |
|  | 135 | <u>236</u> | <u>251</u> | 185 | 195 | 263 | <u>219</u> | <u>237</u> | <u>214</u> | <u>257</u> |
| A-2304 | <u>125</u> | <u>236</u> | <u>239</u> | <u>179</u> | <u>195</u> | 251 | <u>219</u> | <u>229</u> | <u>204</u> | <u>251</u> |
|  | 133 | 238 | <u>251</u> | 179 | 203 | <u>255</u> | <u>219</u> | <u>237</u> | <u>214</u> | <u>257</u> |

Underlined alleles are common to both profiles.

*The 6 markers indicated by an asterisk (*) have been adopted by the EU Grape Genetic Resources Working Group and Foundation Plant Services as common markers to facilitate exchange of data among grape research laboratories.

Allele Sizes in Base Pairs for 10 Microsatellite DNA Markers

The base pair numbers used to designate grape microsatellite alleles may differ slightly between laboratories because of differences in methodology. Adjustments for inter-laboratory differences can be made by comparing profiles of common cultivars. The Plant Identification Lab's reference profiles for several cultivars are provided for this purpose in Table 5.

TABLE 5

Reference Profiles

| Cultivar | VVS2* | VVMD5* | VVMD7* | VVMD27* | VrZAG62* | VrZAG79* | VVMD6 | VVMD28 | VVMD31 | VVMD32 |
|---|---|---|---|---|---|---|---|---|---|---|
| Chardonnay | 137 | 234 | 239 | 181 | 189 | 243 | 205 | 221 | 214 | 241 |
|  | 143 | 238 | 243 | 189 | 197 | 245 | 214 | 231 | 216 | 273 |
| Cabernet Sauvignon | 139 | 232 | 239 | 175 | 189 | 247 | 211 | 237 | 206 | 241 |
|  | 151 | 240 | 239 | 189 | 195 | 247 | 212 | 239 | 210 | 241 |
| Muscat Of Alexandria | 133 | 228 | 249 | 179 | 187 | 247 | 194 | 247 | 216 | 265 |
|  | 149 | 232 | 251 | 194 | 205 | 255 | 214 | 271 | 224 | 273 |
| Thompson Seedless | 145 | 234 | 239 | 181 | 189 | 247 | 212 | 221 | 212 | 251 |
|  | 151 | 234 | 253 | 194 | 189 | 259 | 214 | 247 | 212 | 251 |
| Zinfandel | 133 | 226 | 247 | 179 | 201 | 237 | 212 | 251 | 212 | 257 |
|  | 143 | 236 | 249 | 181 | 205 | 259 | 214 | 261 | 214 | 265 |

DEPOSIT INFORMATION

A deposit of the Board of Trustees of the University of Arkansas of grape plant 'Compassion' disclosed above and recited in the appended claims has been made with the Provasoli-Guillard National Center for Marine Algae & Microbiota (Bigelow Laboratory for Ocean Sciences; hereinafter "Bigelow Lab"), 60 Bigelow Drive, East Boothbay, Me. 04544. The date of deposit was Feb. 21, 2023. The deposit of a tissue culture sample was taken from the same deposit maintained by the University of Arkansas Division of Agriculture Rice Research and Extension Center (2900 Hwy 130 E., Stuttgart, Ark. 72160) since prior to the filing date of this application. All restrictions will be irrevocably removed upon granting of a patent, and the deposit is intended to meet all of the requirements of 37 C.F.R. §§ 1.801-1.809. The Accession Number provided by Bigelow lab is 202302014. The deposit will be maintained in the depository for a period of thirty years, or five years after the last request, or for the enforceable life of the patent, whichever is longer, and will be replaced as necessary during that period.

I claim:

1. A grape plant or an asexually reproduced progeny thereof designated as 'Compassion', of which a tissue culture sample is deposited under Accession No. 202302014.

2. A grape plant comprising all of the physiological and morphological characteristics of the grape plant of claim 1.

3. The grape plant of claim 1, wherein the grape plant comprises the microsatellite alleles identified in the following table:

| Microsatellite DNA Marker | Allele 1 | Allele 2 |
|---|---|---|
| VVS2 | 125 | 135 |
| VVMD5 | 232 | 236 |
| VVMD7 | 239 | 251 |
| VVMD27 | 179 | 185 |
| VrZAG62 | 195 | 195 |
| VrZAG79 | 255 | 263 |

4. The grape plant of claim 3, further comprising the microsatellite alleles identified in the following table:

| Microsatellite DNA Marker | Allele 1 | Allele 2 |
|---|---|---|
| VVMD6 | 219 | 219 |
| VVMD28 | 229 | 237 |
| VVMD31 | 204 | 214 |
| VVMD32 | 251 | 257 |

5. A grape plant clonally propagated from the grape plant of claim 1.

6. A transgenic grape plant comprising the grape plant of claim 1 and further comprising a exogenous polynucleotide, wherein the exogenous polynucleotide optionally confers resistance to a herbicide, a pest, an insect, or a disease.

7. A grape plant part obtained from the grape plant of claim 1.

8. The grape plant part of claim 7, wherein the grape plant part is a plant cell.

9. A pollen of the grape plant of claim 1.

10. An ovule of the grape plant of claim 1.

11. A tissue culture of cells produced from a protoplast or a cell from the grape plants, or parts thereof, of claim 1, wherein the protoplast or the cell is optionally produced from a plant part selected from the group consisting of a pollen, an ovule, an embryo, a leaf, a stem, a root, a root tip, an anther, a cotyledon, a meristematic cell, a hypocotyl, a pistil, a flower, and a fruit.

12. A method for producing a grape plant comprising:
crossing the grape plant designated as 'Compassion', of which a tissue culture sample is deposited under Accession No. 202302014, with itself or a second grape plant, and
harvesting the resultant seed or embryo.

13. The method of claim 12, further comprising growing the seed or embryo into a mature grape plant.

14. The method of claim 12, wherein the crossing is performed by the application of a pollen of the grape plant designated as 'Compassion' to an ovule of the second grape plant or wherein the crossing is performed by the application of a pollen of the second grape plant to an ovule of the grape plant designated as 'Compassion'.

15. The method of claim 14, wherein the resultant embryo is removed from the developing fruit and placed in tissue culture for expansion prior to growing.

16. A method of producing a transgenic grape plant comprising:
introducing a exogenous polynucleotide into the grape plant, or part thereof, of claim 1.

17. A method of producing a grape plant product comprising:
obtaining the grape plant, or part thereof, of claim 1, and producing the grape plant product.

18. The method of claim 17, wherein the grape plant product is selected from the group consisting of grapes, raisins, wine, juice, jam, jelly, paste, puree, freeze-dried fruits, and nutraceutical compositions.

19. A grape plant product comprising fruit of the grape plant designated as 'Compassion', of which a tissue culture sample is deposited under Accession No. 202302014.

20. The grape plant product of claim 19, wherein the grape plant product comprises at least one grape plant cell, or part of the grape plant, designated as 'Compassion'.

* * * * *